United States Patent
Van Asseldonk et al.

(10) Patent No.: US 11,666,688 B2
(45) Date of Patent: Jun. 6, 2023

(54) PUMP DEVICE, COMPRISING A PUMP AND A HOUSING ACCOMMODATING THE PUMP

(71) Applicant: KONINKLIJKE PHILIPS N.V., Eindhoven (NL)

(72) Inventors: Johannes Petrus Antonius Maria Van Asseldonk, Best (NL); Alexander Van Rooijen, Eindhoven (NL); Eyob Atnafu Amra, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 504 days.

(21) Appl. No.: 16/649,709

(22) PCT Filed: Sep. 27, 2018

(86) PCT No.: PCT/EP2018/076210
§ 371 (c)(1),
(2) Date: Mar. 23, 2020

(87) PCT Pub. No.: WO2019/063664
PCT Pub. Date: Apr. 4, 2019

(65) Prior Publication Data
US 2020/0254159 A1 Aug. 13, 2020

(30) Foreign Application Priority Data

Sep. 27, 2017 (EP) .................................. 17193503

(51) Int. Cl.
*A61M 1/06* (2006.01)
*F04B 53/00* (2006.01)
*A61M 1/00* (2006.01)

(52) U.S. Cl.
CPC .............. *A61M 1/06* (2013.01); *A61M 1/064* (2014.02); *A61M 1/80* (2021.05); *F04B 53/003* (2013.01);
(Continued)

(58) Field of Classification Search
CPC ........ A61M 1/06; A61M 1/062; A61M 1/064; A61M 2205/42
See application file for complete search history.

(56) References Cited

U.S. PATENT DOCUMENTS

| | | | |
|---|---|---|---|
| 5,466,229 | A | 11/1995 | Elson |
| 2001/0038799 | A1 | 11/2001 | Silver |

(Continued)

FOREIGN PATENT DOCUMENTS

| | | |
|---|---|---|
| CN | 203763554 | 8/2014 |
| EP | 0595459 | 5/1994 |

(Continued)

OTHER PUBLICATIONS

International Search Report and Written Opinion dated Nov. 30, 2018 for International Application No. PCT/EP2018/076210 Filed Sep. 27, 2018.

*Primary Examiner* — Catharine L Anderson
*Assistant Examiner* — Arjuna P Chatrathi

(57) ABSTRACT

A pump device as may be used in a breast pump assembly including a pump configured to put fluid in motion, a housing accommodating the pump, at least one fluid transporting conduit connected to the pump, the at least one conduit extending between the pump and the housing, thereby connecting the pump to a position at the housing where the housing is provided with at least one opening for allowing fluid to pass, and a mounting arrangement for mounting the pump in the housing. The at least one conduit is part of the mounting arrangement and has flexible properties to reduce an extent to which vibrations of the pump are transferred to the housing through the mounting arrangement during operation of the device.

13 Claims, 3 Drawing Sheets

(52) U.S. Cl.
CPC ....... *A61M 1/0697* (2021.05); *A61M 1/06935* (2021.05); *A61M 2205/42* (2013.01); *A61M 2209/08* (2013.01)

(56) References Cited

U.S. PATENT DOCUMENTS

| | | | | |
|---|---|---|---|---|
| 2004/0127845 | A1* | 7/2004 | Renz | A61M 1/06 604/74 |
| 2007/0292276 | A1* | 12/2007 | Stutz | A61M 1/062 417/54 |
| 2008/0177224 | A1* | 7/2008 | Kelly | A61M 1/06935 604/74 |
| 2010/0010477 | A1 | 1/2010 | Augustine | |
| 2010/0178183 | A1* | 7/2010 | Kaufmann | F04B 53/003 248/638 |
| 2011/0107920 | A1* | 5/2011 | Buhler | A47J 31/46 99/292 |
| 2011/0270162 | A1 | 11/2011 | Guo | |
| 2014/0157956 | A1* | 6/2014 | Date | F04B 39/121 74/99 R |
| 2014/0270728 | A1* | 9/2014 | Date | F04B 53/003 392/394 |
| 2015/0027561 | A1* | 1/2015 | Mauthe | F04D 29/40 137/377 |
| 2016/0067393 | A1 | 3/2016 | Barnes | |
| 2019/0365966 | A1* | 12/2019 | Bächler | A61M 1/80 |

FOREIGN PATENT DOCUMENTS

| | | | |
|---|---|---|---|
| JP | 2000018327 A | * | 1/2000 |
| JP | 2000018327 A | | 1/2000 |
| WO | 2017055109 | | 4/2017 |
| WO | 2017/140562 | | 8/2017 |

\* cited by examiner

PUMP DEVICE, COMPRISING A PUMP AND A HOUSING ACCOMMODATING THE PUMP

CROSS REFERENCE TO RELATED APPLICATIONS

This application is the U.S. National Phase application under 35 U.S.C. § 371 of International Application No. PCT/EP2018/076210 filed Sep. 27, 2018, published as WO 2019/063664 on Apr. 4, 2019, which claims the benefit of European Patent Application Number 17193503.4 filed Sep. 27, 2017. These applications are hereby incorporated by reference herein.

FIELD OF THE INVENTION

The invention relates to a pump device, comprising a pump configured to put fluid in motion, a housing accommodating the pump, at least one conduit connected to the pump and configured to transport fluid to and/or from the pump, the at least one conduit extending between the pump and the housing, thereby connecting the pump to a position at the housing where the housing is provided with at least one opening for allowing fluid to pass, and a mounting arrangement through which the pump is mounted in the housing.

The invention also relates to a breast pump assembly, comprising: (i) an expression kit including a breast-receiving funnel, a milk outlet and an air outlet, (ii) a vacuum unit for realizing a pressure cycle in the breast-receiving funnel of the expression kit, including an air inlet and a pump device as mentioned for sucking air from the breast-receiving funnel, through the air outlet of the expression kit and the air inlet of the vacuum unit, and (iii) a conduit for establishing an air path between the air outlet of the expression kit and the air inlet of the vacuum unit.

BACKGROUND OF THE INVENTION

The background of the invention will now be explained in the context of a breast pump assembly, which should not be understood so as to imply that the invention is limited to that particular context.

In general, a breast pump assembly is a well-known apparatus for extracting milk from a breast of a user, or two breasts simultaneously. Breast pump assemblies may be used in various situations, for example, if a baby or infant is not capable of extracting milk from the breast, or if a mother is separated from her baby or infant and the baby or infant is to be fed with breast milk at a later stage, by the mother or another person. Hence, breast pump assemblies are be used by women to express breast milk at a convenient time, to be stored for later consumption by their/a child. Breast pump assemblies may also be helpful in a situation in which it is desired to stimulate and increase milk production in women with a low milk supply.

A breast pump assembly is typically operated with one or two expression kits. Among other things, an expression kit comprises a breast-receiving funnel for receiving a user's breast, which funnel may be equipped with pads or the like for massaging the breast in a certain way, and is designed for connection to a vacuum unit for realizing a pressure cycle in the breast-receiving funnel, by means of which milk expression from the breast is enabled. In practical cases, the vacuum unit comprises an electric vacuum pump device. The fact is that by generating a pressure cycle, particularly a vacuum cycle, possibly accompanied by a certain way of massaging the breast, a simulation of a feeding action is obtained, which triggers the necessary let-down reflex in the user of the breast pump assembly.

In the field of breast pump assemblies, it is desirable for the vacuum unit to be compact, so that some person moving a breast pump assembly does not need to carry a big machine on the go, and also to be silent during operation, so that a woman using the breast pump assembly is not disturbed by noise during a milk expression process. However, it appears in practice that the pump device of the breast pump assembly causes quite a lot of noise. The fact is that the pump device comprises a housing in which the pump is mounted, and when the pump device is operated, vibrations are transferred from the pump to the housing through a mounting arrangement interconnecting the pump and the housing. Another factor contributing to noise generation is the fact that one or more conduits as present inside the housing for connecting the pump to a position at the housing where the housing is provided with at least one opening for allowing air to pass are also made to vibrate when the pump is operated. The conduits are short so as to limit dead volume, which is beneficial to vacuum performance of the pump device. Furthermore, using short conduits helps to keep sizes limited and also involves ease of assembly. However, a disadvantage of the known design of the conduits is that the conduits are rather stiff so that the effect that vibrations of the pump are imposed on the conduits is quite strong. Vibration of the conduits may even cause a rattling noise to be generated, namely when the conduits touch the housing and/or other internal parts of the pump device.

It is an object of the invention to provide a pump device of a new design, particularly a new design that involves less noise generation during operation of the pump device than existing designs, without deteriorating the pumping functionality of the pump device, and without necessitating an increase of size of the pump device.

SUMMARY OF THE INVENTION

In view of the foregoing, the invention provides a pump device, comprising a pump configured to put fluid in motion, a housing accommodating the pump, at least one conduit connected to the pump and configured to transport fluid to and/or from the pump, the at least one conduit extending between the pump and the housing, thereby connecting the pump to a position at the housing where the housing is provided with at least one opening for allowing fluid to pass, and a mounting arrangement through which the pump is mounted in the housing, wherein the at least one conduit is part of the mounting arrangement and has flexible properties so as to reduce an extent to which vibrations of the pump are transferred to the housing through the mounting arrangement during operation of the pump device.

According to the invention, the at least one conduit of the pump device is made part of the mounting arrangement through which the pump is mounted in the housing. Hence, in the pump device according to the invention, the at least one conduit has a main function of transporting fluid to and/or from the pump, and an auxiliary function of mounting the pump in the housing, i.e. a combined functionality which may contribute to compactness of design. Further, the at least one conduit has flexible properties so as to reduce an extent to which vibrations of the pump are transferred to the housing through the mounting arrangement during operation of the pump device. For example, the at least one conduit may be made of silicone, nitrile rubber (NBR), or a thermoplastic elastomer (TPE). It is noted that the term "flexible" is to be understood for its generally known meaning, wherein an ability of the at least one conduit to deform elastically and return to an original shape when applied stress is removed is covered by the term "flexible properties".

The pump of the device may be designed to pump air, as is the case in the context of breast pump assemblies, and may be a vacuum pump, for example. However, the invention is not limited to the type of fluid that may be displaced by means of the pump. For instance, the pump may be suitable for pumping water or other liquids.

The mounting arrangement through which the pump is mounted in the housing may be realized in any suitable manner. It may be practical for the mounting arrangement to further comprise at least one resilient supporting member extending between the pump and the housing, aside from the at least one conduit. Such a resilient supporting member may comprise a spring, for example. Within the framework of the invention, a design of the pump device is feasible in which the mounting arrangement comprises a coil spring that is arranged so as to extend between the pump and the housing, at a side of the pump that is intended to be a bottom side in a normal, operational orientation of the pump device. It may be so that the pump is mounted in the housing through no more than one conduit and one resilient supporting member. In such a case, it may be advantageous for the resilient supporting member to be coupled to the pump at a position on the pump associated with the mass center of the pump, so as to guarantee mounting stability. When the resilient supporting member is provided at the bottom side of the pump, as mentioned, a position on the pump associated with the mass center of the pump is a position at the bottom of the pump, vertically underneath the mass center of the pump.

It is very well possible for the pump device according to the invention to comprise at least two conduits which are part of the mounting arrangement and have flexible properties so as to reduce an extent to which vibrations of the pump are transferred to the housing through the mounting arrangement during operation of the pump device. In case the pump is intended to be used for pumping air, for example, one of the at least two conduits may be connected to an air inlet of the pump, and the other of the at least two conduits may be connected to an air outlet of the pump. Using at least two conduits in the mounting arrangement may help in dampening vibrations in all directions of freedom. It may be advantageous if the at least two conduits of the mounting arrangement are identical parts, i.e. are of identical design, having the same shape and size, and being made of the same material(s).

In the case that the pump device comprises at least two conduits which are part of the mounting arrangement and have flexible properties so as to reduce an extent to which vibrations of the pump are transferred to the housing through the mounting arrangement during operation of the pump device, it may be so that the pump is mounted in the housing through no more than two conduits. Not using one or more additional components for the mounting arrangement contributes to simplicity of design. On the other hand, it may be so that the pump is mounted in the housing through no more than two conduits and one resilient supporting member. As mentioned, when one resilient supporting member is used, it may be advantageous for the resilient supporting member to be coupled to the pump at a position on the pump associated with the mass center of the pump.

In general, the at least one conduit may be of any suitable design, and may have a straight or curved appearance, for example. According to a feasible possibility, the at least one conduit may comprise an elbow piece.

As mentioned, the pump of the pump device according to the invention may be a vacuum pump. In that case, as known in the art, the pump may typically comprise an assembly of a motor and a solenoid valve.

Assuming that the pump comprises an electric power supply member, it may be so that the electric power supply member is part of the mounting arrangement and has flexible properties so as to reduce an extent to which vibrations of the pump are transferred to the housing through the mounting arrangement during operation of the pump device. When this option is put to practice, the electric power supply member is provided with an auxiliary functionality besides the main functionality thereof, namely a mounting functionality besides the electric power supply functionality thereof. The electric power supply member may comprise an electrically conductive cable or strip, for example. In any case, the electric power supply member may be of elongated shape and may be spirally wound, at least along a part thereof, particularly a part located inside the housing, in order to be capable of fulfilling the mounting functionality with a certain level of resilience. In the feasible case that the electric power supply member comprises a metal strip, the metal strip may be designed such as to act like a kind of leaf spring, for example.

The above-described and other aspects of the invention will be apparent from and elucidated with reference to the following detailed description of a conventional pump device, a number of embodiments of a pump device according to the invention, and a breast pump assembly that is equipped with a pump device according to the invention.

BRIEF DESCRIPTION OF THE DRAWINGS

The invention will now be explained in greater detail with reference to the figures, in which equal or similar parts are indicated by the same reference signs, and in which.

DETAILED DESCRIPTION OF EMBODIMENTS

The invention is in the field of pump devices, particularly pump devices comprising a housing in which the actual pump is accommodated, and comprising at least one conduit that is connected to the pump and that is configured to enable transport of fluid to and/or from the pump.

Figure 1:
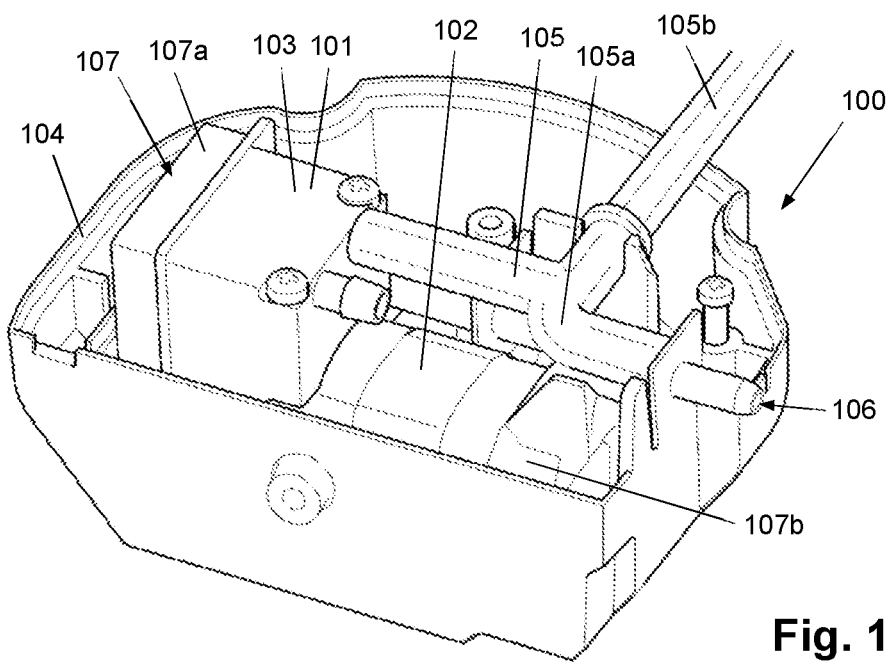
FIG. 1 diagrammatically shows a perspective view of a conventional pump device, with a part of a housing of the pump device removed.

In FIG. 1, a conventional pump device 100 is shown, in order to address some general aspects of a pump device, and also to provide insight in some disadvantageous aspects of the design according to the state of the art.

In the first place, the pump device 100 comprises a pump 101. In the shown example, the pump 101 is a micro vacuum pump that is configured to realize a vacuum cycle in a unit as may be connected to the pump 101. Hence, the pump 101 is configured to displace air, mainly to suck air from a unit as may be connected to the pump 101. Micro vacuum pumps are very well suitable to be used in consumer appliances, and a unit to be connected to the pump 101 may be a breast-receiving funnel of a breast pump assembly, to mention one of many feasible examples. The pump 101 as shown in FIG. 1 is of the type comprising an electric motor 102 and a solenoid valve 103.

In the second place, the pump device 100 comprises a plastic housing 104 accommodating the pump 101. In FIG. 1, only a bottom part of the housing 104 is shown, while a top part of the housing 104 is omitted from the figure so as to enable a view on the pump 101 and other internal components located inside the housing 104. The other internal components comprise a conduit 105 that is connected to the pump 101 and that is shaped like a manifold having two branches 105a, 105b. It is clearly illustrated in FIG. 1 that one of the branches 105a, 105b extends between the pump 101 and a position at the bottom part of the housing 104 where the housing 104 is provided with an opening 106 for allowing air to pass. In particular, the pump 101 is connected to that position at the housing 104 through the respective branch 105a of the conduit 105. In general, the conduit 105 serves for transporting air to and/or from the pump 101. One possible air path between the pump 101 and a position outside of the housing 104 is established through the conduit 105 and the opening 106 in the housing 104.

The pump 101 is mounted in the housing 104 through a mounting arrangement 107 that comprises two rigid plastic cap-like members 107a, 107b which are arranged at either side of the pump 101 so that the pump 101 is sandwiched between them, and which are attached to the housing 104. In this way, a robust attachment of the pump 101 to the housing 104 is obtained, in a relatively simple and cheap manner. However, according to an insight underlying the invention, such a design of the mounting arrangement 107 is not favorable as far as noise generation during operation of the pump device 100 is concerned. It appears that vibrations of the pump 101, caused by the motor 102, are transferred to the housing 104 through the cap-like members 107a, 107b. To make things worse, the conduit 105 also appears to play a role in transmitting such vibrations to the housing 104.

The invention is aimed at taking noise reducing measures, and resides in not simply adding one or more damping members or the like at an appropriate position, but providing a whole new design of a pump device, as will now be explained on the basis of FIGS. 2-4 which relate to three possible variants of a pump device according to the invention.

Figure 2:
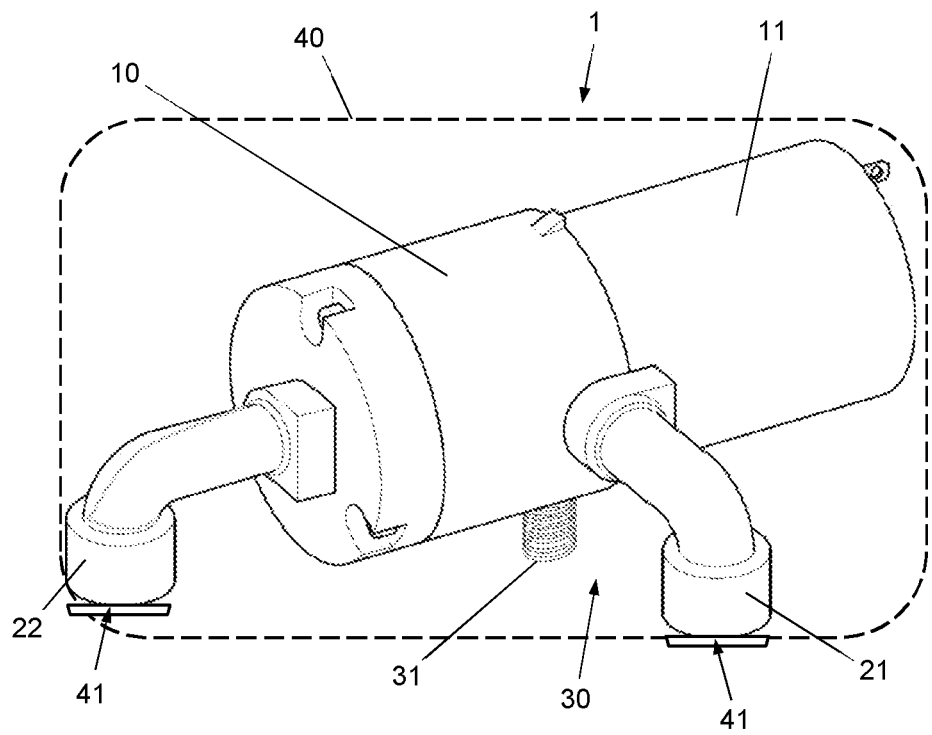
FIG. 2 diagrammatically shows a perspective view of a pump and two conduits and a supporting spring coupled to the pump; the pump, the conduits and the supporting spring being part of a pump device according to a first embodiment of the invention.
Figure 3:
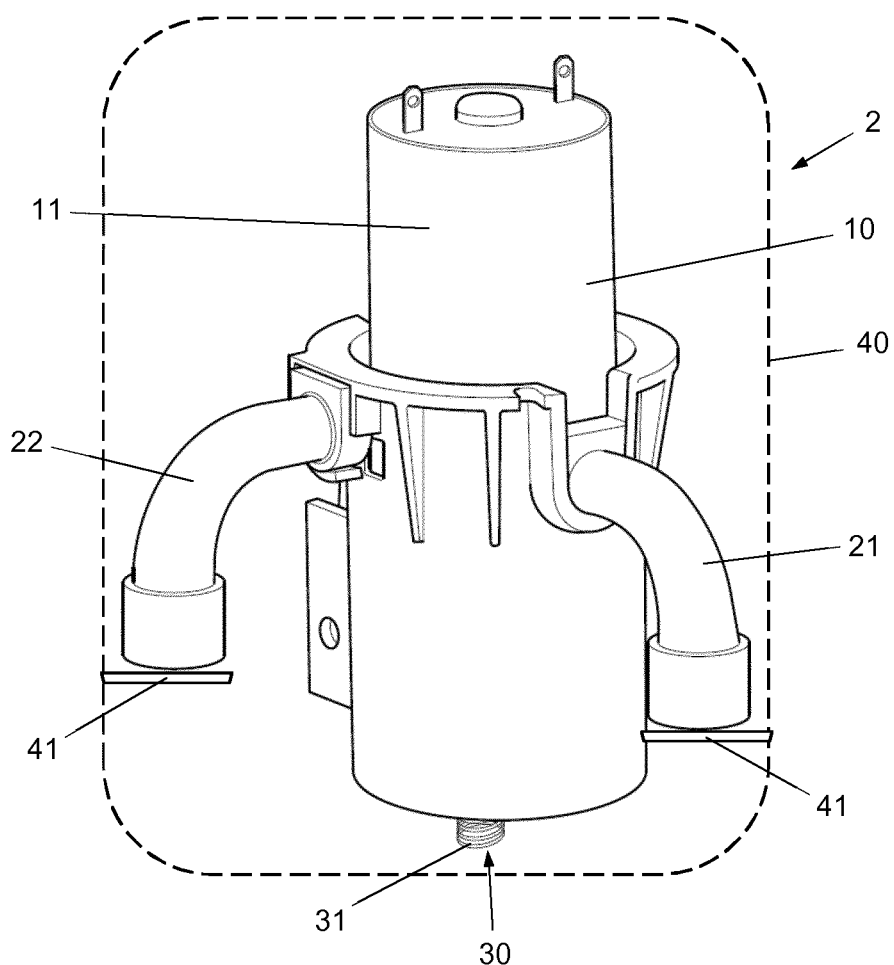
FIG. 3 diagrammatically shows a perspective view of a pump and two conduits and a supporting spring coupled to the pump; the pump, the conduits and the supporting spring being part of a pump device according to a second embodiment of the invention.

FIGS. 2 and 3 relate to a pump device 1, 2 according to a first embodiment of the invention and a second embodiment of the invention, respectively, and show a pump 10 and two conduits 21, 22 and a supporting spring 31 coupled to the pump 10, which are all part of the two respective embodiments. FIG. 4 relates to a pump device 3 according to a third embodiment of the invention, and shows a pump 10 and a conduit 21, an electric power supply wire 32 and a supporting spring 31 coupled to the pump 10, which are all part of the embodiment. Like the conventional pump device 100, the pump device 1, 2, 3 according to the invention comprises a housing 40 for accommodating the components as mentioned, but such a housing 40 is only diagrammatically shown in FIGS. 2-4 as a dashed box for the sake of clarity of illustration.

Figure 4:
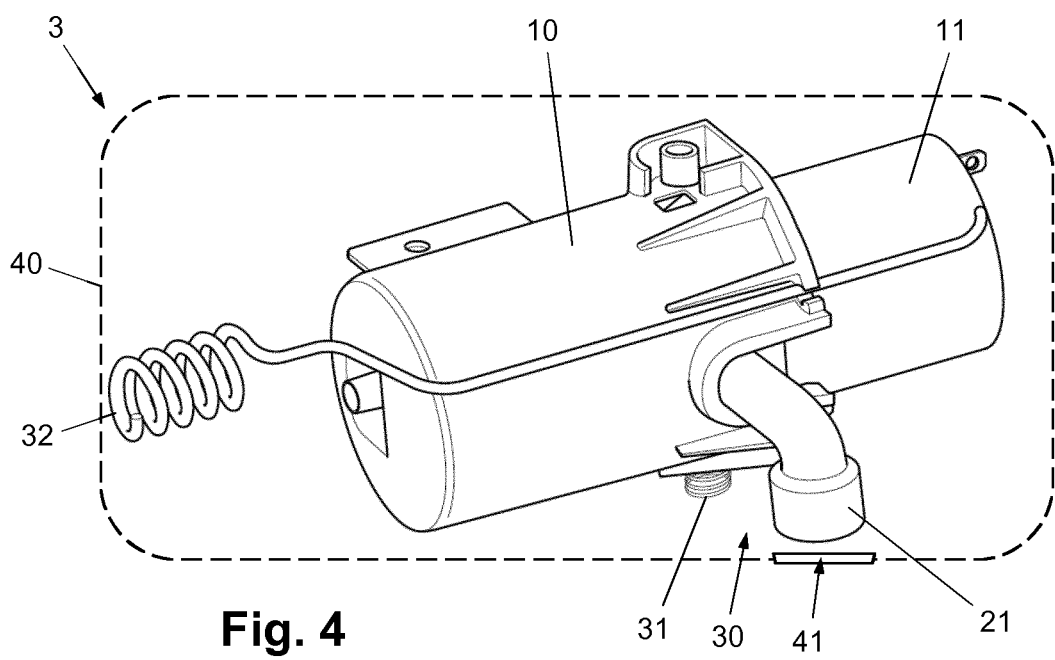
FIG. 4 diagrammatically shows a perspective view of a pump and a conduit, an electric power supply wire and a supporting spring coupled to the pump; the pump, the conduit, the electric power supply wire and the supporting spring being part of a pump device according to a third embodiment of the invention.

The pumps 10 as shown in FIGS. 2-4 are micro vacuum pumps comprising an electric motor 11, which are suitable for use in a breast pump assembly, for example, wherein it is possible/practical for the electric motor 11 to be combined with a solenoid valve. The actual possibility of applying a pump device 1, 2, 3 according to the invention in a breast pump assembly will be explained later on the basis of FIG. 5. In this respect, it is emphasized that the invention is not restricted to this particular application of the pump device 1, 2, 3, and also that the pump device 1, 2, 3 does not need to be a vacuum pump of some sort. The invention covers many types of pump devices and many possible applications of pump devices. The pump device may be a mini water pump for use in a coffee maker, to mention one of many feasible examples existing within the framework of the invention.

In the pump devices 1, 2 according to the first embodiment and the second embodiment of the invention, respectively, the conduits 21, 22 and the supporting spring 31 are part of a mounting arrangement 30 for mounting the pump 10 in the housing 40. In fact, the conduits 21, 22 and the supporting spring 31 may be the only parts of the mounting arrangement 30 as mentioned, although the invention also covers the possibility of the mounting arrangement 30 including more components. Further, it is to be noted that application of the supporting spring 31 is not essential within the framework of the invention.

In respect of the conduits 21, 22, it is noted that each of the conduits 21, 22 is arranged so as to extend between the pump 10 and the housing 40, particularly a position at the housing 40 where the housing 40 is provided with at least one opening 41 (only diagrammatically depicted in FIGS. 2-4) for allowing air to pass, thereby connecting the pump 10 to that position at the housing 40. In this arrangement, the conduits 21, 22 have both a function in transporting air to and/or from the pump 10 and a function in suspending the pump 10 from the housing 40. As illustrated in FIG. 2, one of the conduits 21, 22 may particularly be arranged for letting out air from the pump 10, for example. In the shown examples, the conduits 21, 22 are identical, and comprise an elbow piece. It may be advantageous if the elbow piece is a 90° elbow piece, as is the case in the shown examples. The conduits 21, 22 comprise flexible material and are preferably arranged so as to realize flexibility in the mounting arrangement 30 in all six degrees of freedom.

In respect of the supporting spring 31, it is noted that this may be a coil spring, as shown, or any other type of spring that is suitable for coupling the pump 10 to the housing 40. Preferably, the supporting spring 31 is arranged at a position that is a central position as seen with regard to the mass center of the pump 10 so as to contribute optimally to mounting stability of the pump 10 in the housing 40. FIG. 2 shows the pump 10 in a generally horizontal orientation, and FIG. 3 shows the pump 10 in a generally vertical orientation. Hence, it follows from a comparison between FIGS. 2 and 3 that the pump 10 can be arranged in different orientations. In each of the possible cases, however, the supporting spring 31 is located at a central position as mentioned earlier, at a side of the pump 10 that is a bottom side in the respective orientation.

On the basis of the fact that the conduits 21, 22 have an auxiliary function in mounting the pump 10 in the housing 40, the mounting arrangement 30 comes with a minimum number of additional components only, namely just one in the shown example, in the form of the supporting spring 31. Also, the design of the pump device 2, 3 according to the invention is simplified with respect to the design of the conventional pump device 100. Transfer of vibrations from the pump 10 to the housing 40 only occurs at well-defined positions, wherein the vibrations are dampened to a considerably extent as an advantageous consequence of the resilient properties of the supporting spring 31 and the flexible properties of the conduits 21, 22.

In the pump device 3 according to the third embodiment of the invention, the conduit 21, the electric power supply wire 32 and the supporting spring 31 are part of a mounting arrangement 30 for mounting the pump 10 in the housing 40. In fact, the conduit 21, the electric power supply wire 32 and the supporting spring 31 may be the only parts of the mounting arrangement 30 as mentioned, although the invention also covers the possibility of the mounting arrangement 30 including more components. As mentioned earlier, application of the supporting spring 31 is not essential within the framework of the invention.

The conduit 21 of the pump device 3 according to the third embodiment of the invention is similar to the conduits 21, 22 as described in the foregoing in the context of the pump devices 1, 2 according to the first embodiment and the second embodiment of the invention, respectively. Further, the supporting spring 31 of the pump device 3 according to the third embodiment of the invention is similar to the supporting spring 31 as described in the foregoing in the context of the pump devices 1, 2 according to the first embodiment and the second embodiment of the invention, respectively.

A notable difference between the pump device 3 according to the third embodiment of the invention and the pump devices 1, 2 according to the first embodiment and the second embodiment of the invention, respectively, resides in the fact that in the pump device 3 according to the third embodiment of the invention, the electric power supply wire 32 is used as a part of the mounting arrangement 30 of the pump device 3. To that end, a part of the electric power supply wire 32, particularly a part of the electric power supply wire 32 located inside the housing 40, is spirally wound so as to have resilience in the electric power supply wire 32. For the sake of completeness, it is noted that within the framework of the invention, the option of attributing a mounting functionality to an electric power supply wire 32 is also applicable to each one of the pump devices 1, 2 according to the first embodiment and the second embodiment of the invention, respectively, and the option of having two conduits 21, 22 and attributing a mounting functionality to both of those conduits 21, 22 is also applicable to the pump device 3 according to the third embodiment of the invention.

As mentioned, one of the possible applications of the pump device 1, 2, 3 according to the invention is an application in an electric breast pump assembly. In view thereof, in the following, a general description of an electric breast pump assembly will be given, with reference to FIG. 5.

A breast pump assembly 200 comprises an expression kit 201 and a vacuum unit 202 for generating a pressure cycle during which vacuum is alternately created and released. The expression kit 201 comprises a functional expression body 203 and a milk receptacle 204 that is connectable to the expression body 203, e.g. by screwing, thereby closing a lower end of the expression body 203. The vacuum unit 202 is an electric vacuum unit and comprises an air inlet 205 and an electric pump device 1, 2, 3 for realizing an alternating vacuum during operation, i.e. during pumping sessions to be performed by means of the breast pump assembly 200. The vacuum unit 202 is only diagrammatically depicted in FIG. 5 as a box, wherein the pump device 1, 2, 3 is represented by a dashed rectangle. For the purpose of operating the pump device 1, 2, 3 in an appropriate and effective manner, the breast pump assembly 200 further comprises a controller (not shown).

Figure 5:
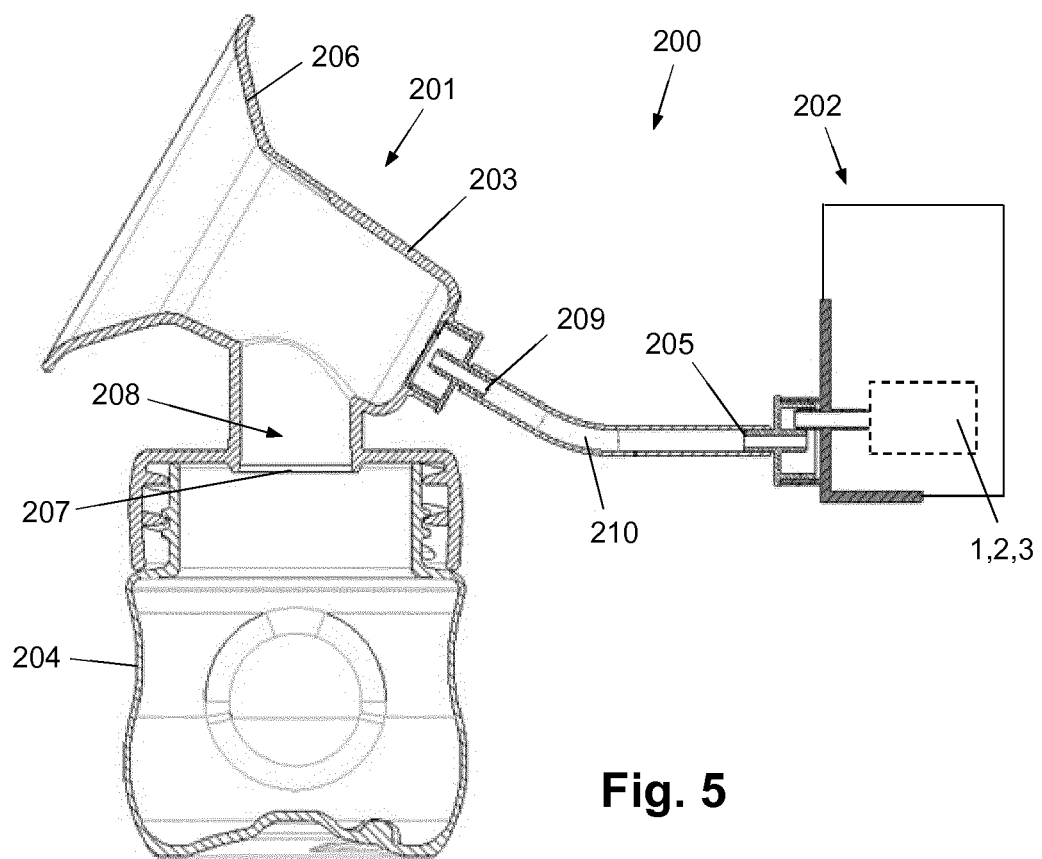
FIG. 5 diagrammatically shows a breast pump assembly that is equipped with a pump device according to the invention.

At the position of the expression body 203, the expression kit 201 comprises a breast-receiving funnel 206 and an aperture acting as a milk outlet 207. The breast-receiving funnel 206 is in fluid communication with the milk outlet 207 through a milk path 208. The breast-receiving funnel 206 can comprise a massage cushion or the like (not shown) for providing a soft and warm feel to the breast and/or imitating a baby's sucking action. Further, at the position of the expression body 203, the expression kit 201 comprises an air outlet 209. In FIG. 5, the breast pump assembly 200 is shown in an assembled condition, in which the air inlet 205 of the vacuum unit 202 is connected to the air outlet 209 of the expression kit 201 through a flexible hose 210. Such a configuration allows for a remote arrangement of the vacuum unit 202 with respect to the expression kit 201, so that the size of that part of the breast pump assembly 200 that is to be applied to a user's breast can be kept within reasonable limits. It is to be noted that the breast pump assembly 200 can comprise two expression kits 201 for enabling a user of the breast pump assembly 200 to extract milk from two breasts at the same time, in which case the expression kits 201 can share a common vacuum unit 202.

General operational aspects of the breast pump assembly 200 will now be mentioned. In the first place, a user makes sure that the expression kit 201 and the vacuum unit 202 are properly connected to each other through the hose 210. Before the vacuum unit 202 is activated, the user furthermore needs to take care that the milk receptacle 204 is properly connected to the expression body 203, and that the breast to be subjected to a milk extraction process is properly inserted into the breast-receiving funnel 206. In that situation, a breast-receiving end of the expression body 203 is sealingly closed by the breast, whereas a lower end of the expression body 203 is sealingly closed by the milk receptacle 204. When, starting from that situation, the vacuum unit 202 is activated, a pressure cycle involving generation and release of vacuum is realized in the expression body 203, as a result of which the breast is subjected to forces which serve for simulating a feeding situation, and as a result of which milk supply is induced from the breast. The breast milk flows from the breast-receiving funnel 206 to the milk receptacle 204 through the milk path 208 and the milk outlet 207, under the influence of gravity and/or the pressure generated by the vacuum unit 202.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details that are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

The invention claimed is:

1. A pump device, comprising:
   a pump configured to put fluid in motion,
   a housing accommodating the pump,
   at least one conduit connected to the pump and configured to transport fluid to and/or from the pump, the at least one conduit extending between the pump and the housing, thereby connecting the pump to a position at the housing where the housing is provided with at least one opening for allowing fluid to pass, and
   a mounting arrangement through which the pump is mounted in the housing without a sub-frame,
   wherein the at least one conduit is part of the mounting arrangement and has flexible properties so as to reduce an extent to which vibrations of the pump are transferred to the housing through the mounting arrangement during operation of the pump device,
   wherein the mounting arrangement further comprises at least one resilient supporting member extending between the pump and the housing, aside from the at least one conduit.

2. The pump device according to claim 1, wherein the at least one resilient supporting member comprises a spring.

3. The pump device according to claim 1, wherein the pump is mounted in the housing through no more than one conduit and one resilient supporting member.

4. The pump device according to claim 3, wherein the resilient supporting member is coupled to the pump at a position on the pump associated with the mass center of the pump.

5. The pump device according to claim 1, wherein the at least one conduit comprises an elbow piece.

6. The pump device according to claim 1, wherein the pump is a vacuum pump comprising an assembly of a motor and a solenoid valve.

7. The pump device according to claim 1, comprising an electric power supply member that is part of the mounting arrangement and has flexible properties so as to reduce an extent to which vibrations of the pump are transferred to the housing through the mounting arrangement during operation of the pump device.

8. The pump device according to claim 7, wherein the electric power supply member is of elongated shape and is at least partially spirally wound.

9. A breast pump assembly, comprising:
   an expression kit including a breast-receiving funnel, a milk outlet and an air outlet,
   a vacuum unit for realizing a pressure cycle in the breast-receiving funnel of the expression kit, including an air inlet and a pump device according to claim 1 for sucking air from the breast-receiving funnel, through the air outlet of the expression kit and the air inlet of the vacuum unit, and
   a conduit for establishing an air path between the air outlet of the expression kit and the air inlet of the vacuum unit.

10. A pump device, comprising:
    a pump configured to put fluid in motion,
    a housing accommodating the pump,
    at least one conduit connected to the pump and configured to transport fluid to and/or from the pump, the at least one conduit extending between the pump and the housing, thereby connecting the pump to a position at the housing where the housing is provided with at least one opening for allowing fluid to pass, and
    a mounting arrangement through which the pump is mounted in the housing,
    the mounting arrangement consisting essentially of at least one of the at least one conduit, at least one spring extending between a central position of the pump and the housing and an electric power supply member,
    wherein the mounting arrangement has flexible properties so as to reduce an extent to which vibrations of the pump are transferred to the housing through the mounting arrangement during operation of the pump device.

11. A pump device, comprising:
    a pump configured to put fluid in motion,
    a housing accommodating the pump,
    at least one conduit connected to the pump and configured to transport fluid to and/or from the pump, the at least one conduit extending between the pump and the housing, thereby connecting the pump to a position at the housing where the housing is provided with at least one opening for allowing fluid to pass, and
    a mounting arrangement through which the pump is mounted in the housing without a sub-frame,
    wherein the at least one conduit is part of the mounting arrangement and has flexible properties so as to reduce an extent to which vibrations of the pump are transferred to the housing through the mounting arrangement during operation of the pump device, and
    wherein the pump is mounted in the housing through no more than one or more of a first conduit, and a second conduit and one resilient supporting member.

12. The pump device according to claim 11, wherein the resilient supporting member is coupled to the pump at a position on the pump associated with the mass center of the pump.

13. The pump device according to claim 11, wherein at least two conduits of the mounting arrangement are identical parts.

* * * * *